(12) United States Patent
Owens

(10) Patent No.: US 7,106,190 B1
(45) Date of Patent: Sep. 12, 2006

(54) CHILD POSITION MONITORING SYSTEM

(76) Inventor: Larry D. Owens, 7530 N. Ridge Blvd., Unit 1E, Chicago, IL (US) 60645

( * ) Notice: Subject to any disclaimer, the term of this patent is extended or adjusted under 35 U.S.C. 154(b) by 16 days.

(21) Appl. No.: 10/784,862

(22) Filed: Feb. 23, 2004

(51) Int. Cl.
*G08B 1/08* (2006.01)

(52) U.S. Cl. .............. 340/539.15; 340/531; 340/572.1; 340/568.1; 340/573.1; 200/61.45 R; 600/390; 600/534

(58) Field of Classification Search .......... 340/539.15, 340/573.1, 573.4, 573.7, 573.3, 575, 517, 340/521, 568.1, 65, 666, 665, 531, 572.1; 600/323, 534, 390; 200/61.45 R, 61.52
See application file for complete search history.

(56) References Cited

U.S. PATENT DOCUMENTS

| | | | |
|---|---|---|---|
| 4,785,291 A | 11/1988 | Hawthorne | |
| 4,862,144 A * | 8/1989 | Tao | 340/573.1 |
| 5,241,300 A * | 8/1993 | Buschmann | 340/573.1 |
| 5,505,199 A * | 4/1996 | Kim | 600/323 |
| 5,510,771 A | 4/1996 | Marshall | |
| 5,525,967 A | 6/1996 | Azizi et al. | |
| 5,727,562 A * | 3/1998 | Beck | 600/534 |
| 5,914,660 A * | 6/1999 | Mesibov et al. | 340/573.7 |
| 5,928,157 A * | 7/1999 | O'Dwyer | 600/534 |
| 6,078,260 A * | 6/2000 | Desch | 340/573.1 |
| 6,127,931 A | 10/2000 | Mohr | |
| 6,356,203 B1 * | 3/2002 | Halleck et al. | 340/689 |
| 6,396,403 B1 | 5/2002 | Haner | |
| 6,765,489 B1 * | 7/2004 | Ketelhohn | 340/573.1 |

* cited by examiner

*Primary Examiner*—Davetta W. Goins

(57) ABSTRACT

A child position monitoring system for providing a warning to a user that a child being monitored has or is moving. The child position monitoring system includes a motion detection assembly detects when the child rolls over, the motion detection assembly includes a transmitter assembly for sending a signal associated with motion detected; a coupling assembly is used for coupling the motion detection assembly to the child; and a monitoring assembly operationally interacting with the motion detection assembly and providing an indication associated with motion detected by the motion detection assembly to the user.

18 Claims, 5 Drawing Sheets

CHILD POSITION MONITORING SYSTEM

BACKGROUND OF THE INVENTION

1. Field of the Invention

The present invention relates to baby monitors and more particularly pertains to a new child position monitoring system for providing a warning to a user that a child being monitored has or is moving.

2. Description of the Prior Art

The use of baby monitors is known in the prior art. Illustrative examples include: U.S. Pat. No. 4,785,291; U.S. Pat. No. 5,510,771; U.S. Pat. No. 5,525,967; U.S. Pat. No. 6,127,931; and U.S. Pat. No. 6,396,403.

Additionally, pressure-matt type devices have been used to monitor children at risk for SIDS or with a sleep apnea problem. Further, various walkie-talkie type audio monitors and video monitors have been used.

While these devices fulfill their respective, particular objectives and requirements, the need remains for a system that can be used regardless of the location used to lay down the child including beds, couches, cribs, floors, etc.

SUMMARY OF THE INVENTION

The present invention meets the needs presented above by providing a motion detecting assembly which can be coupled to or worn by the child. As the child rolls, the motion detection assembly detects the movement of the child and can relay a signal to a user.

Another advantage of the present invention is to provide a new child position monitoring system that allows a parent to have a child sleep on the same bed, couch, or other surface as the parent and be alerted in the child rolls towards the edge of the bed or couch.

To this end, the present invention generally comprises a motion detection assembly detects when the child rolls over, the motion detection assembly includes a transmitter assembly for sending a signal associated with motion detected; a coupling assembly is used for coupling the motion detection assembly to the child; and a monitoring assembly operationally interacting with the motion detection assembly and providing an indication associated with motion detected by the motion detection assembly to the user.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
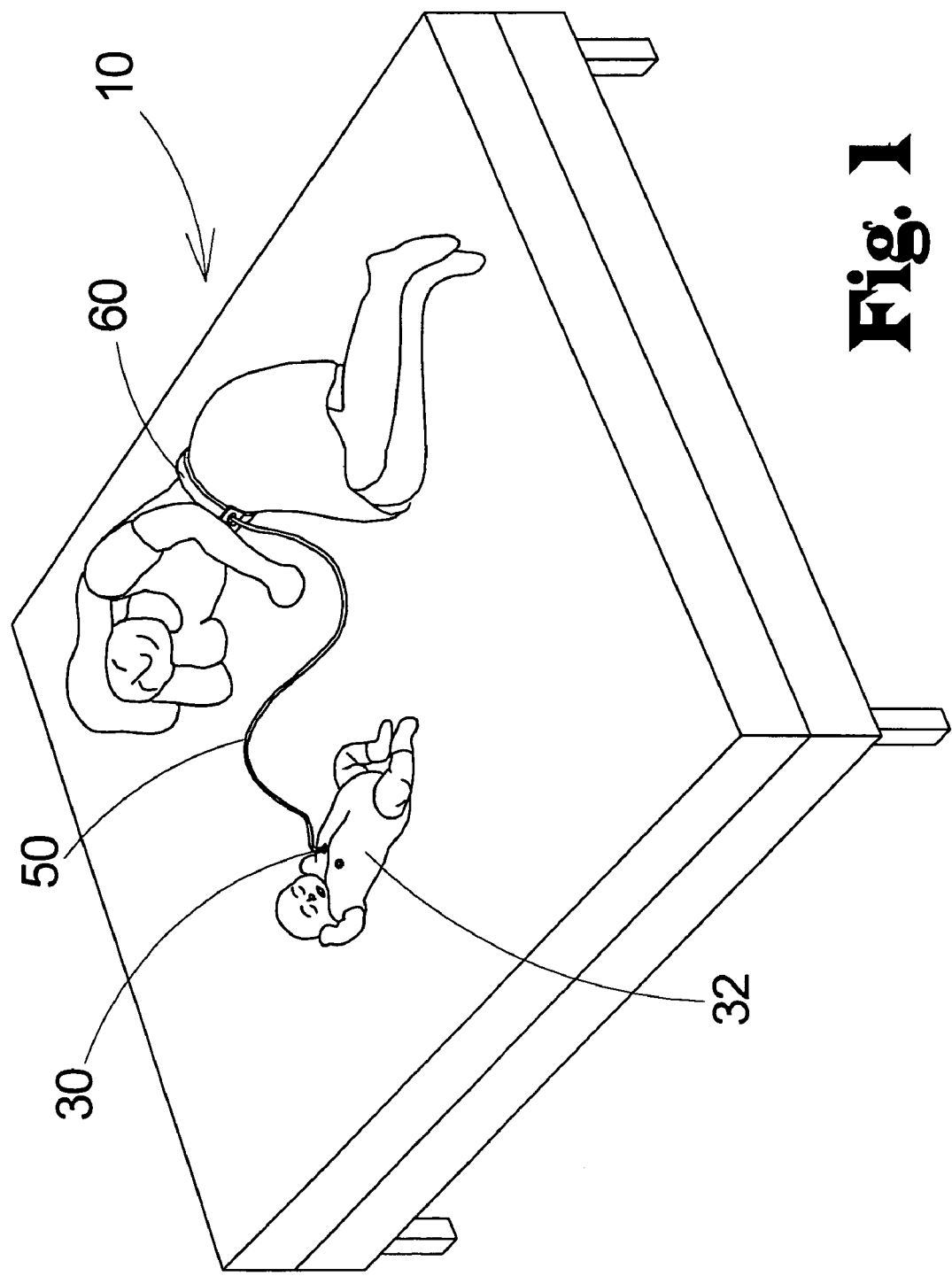
FIG. 1 is a schematic perspective view of a new child position monitoring system in use according to the present invention.
Figure 2:
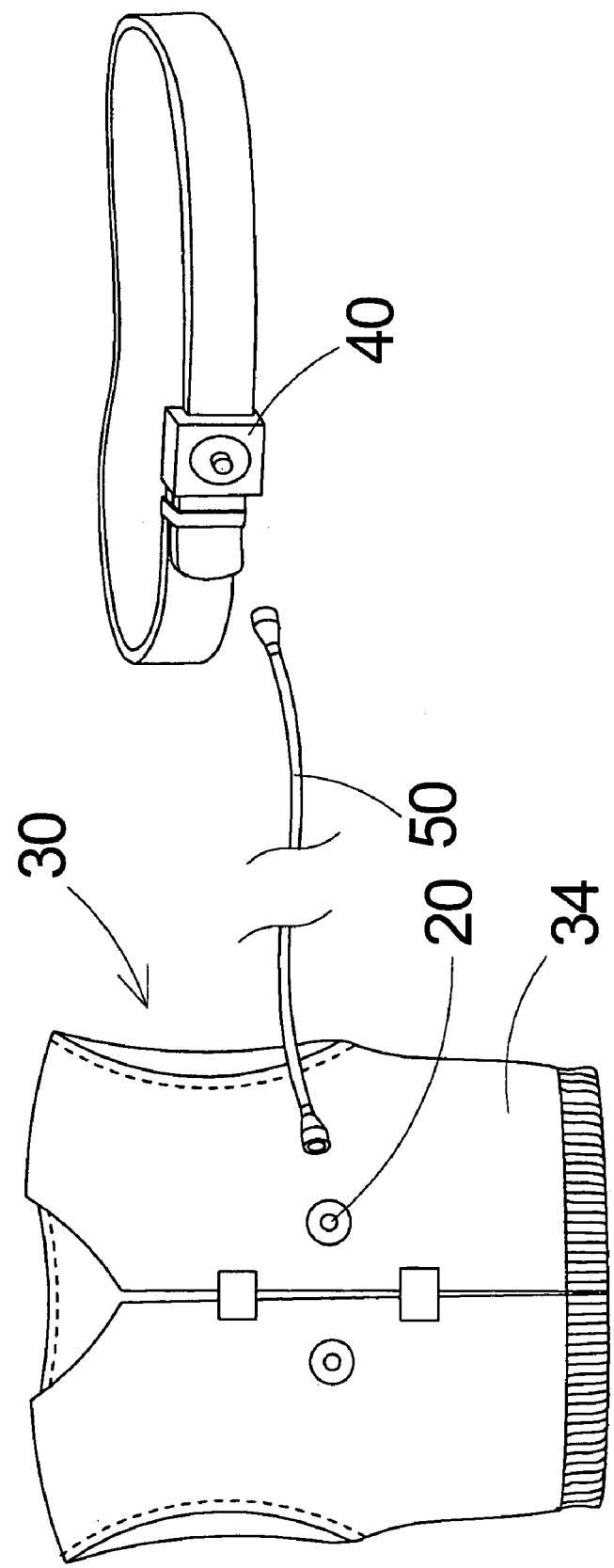
FIG. 2 is a schematic perspective view of the present invention.
Figure 3:
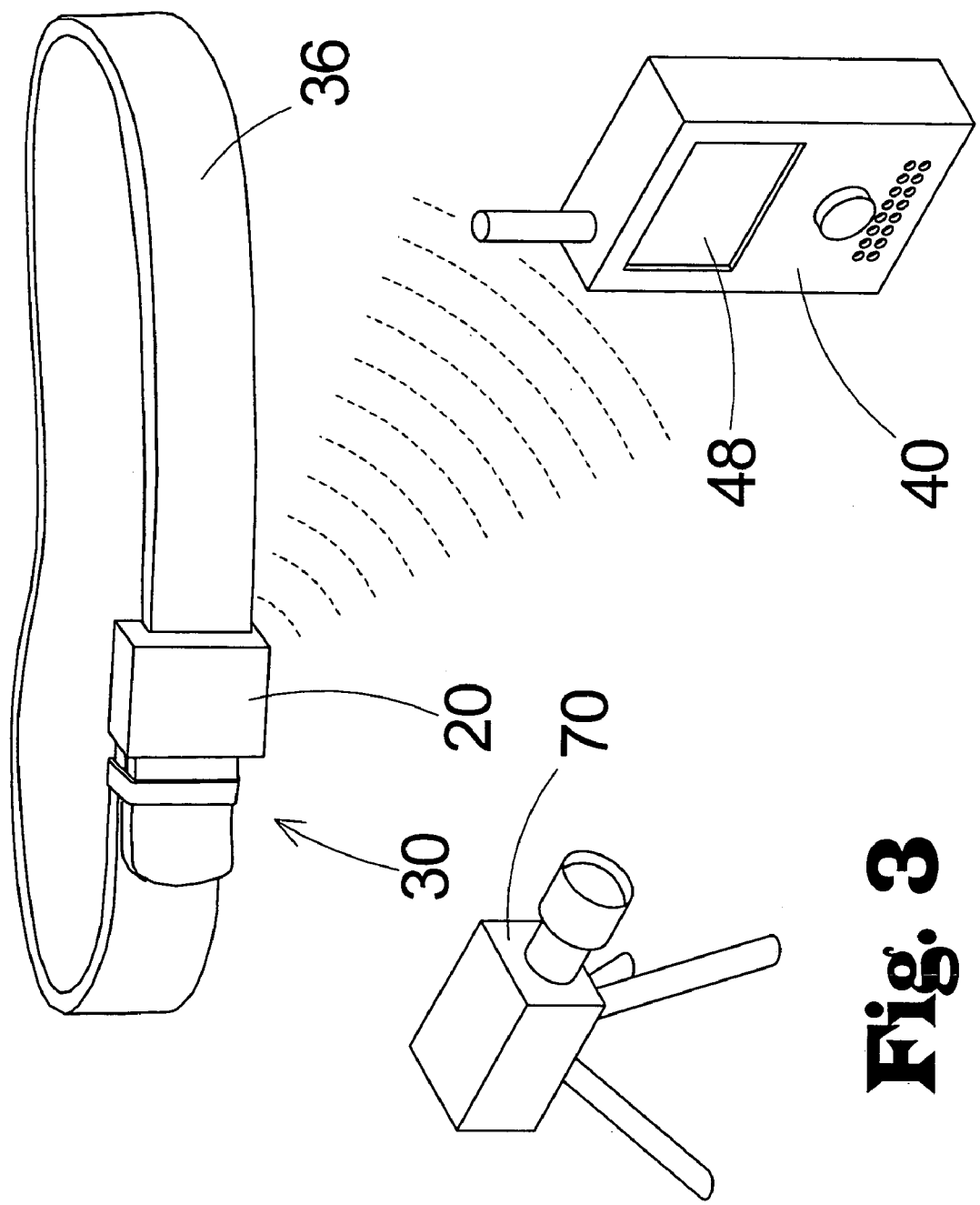
FIG. 3 is a schematic perspective view of an embodiment of the present invention.
Figure 4:
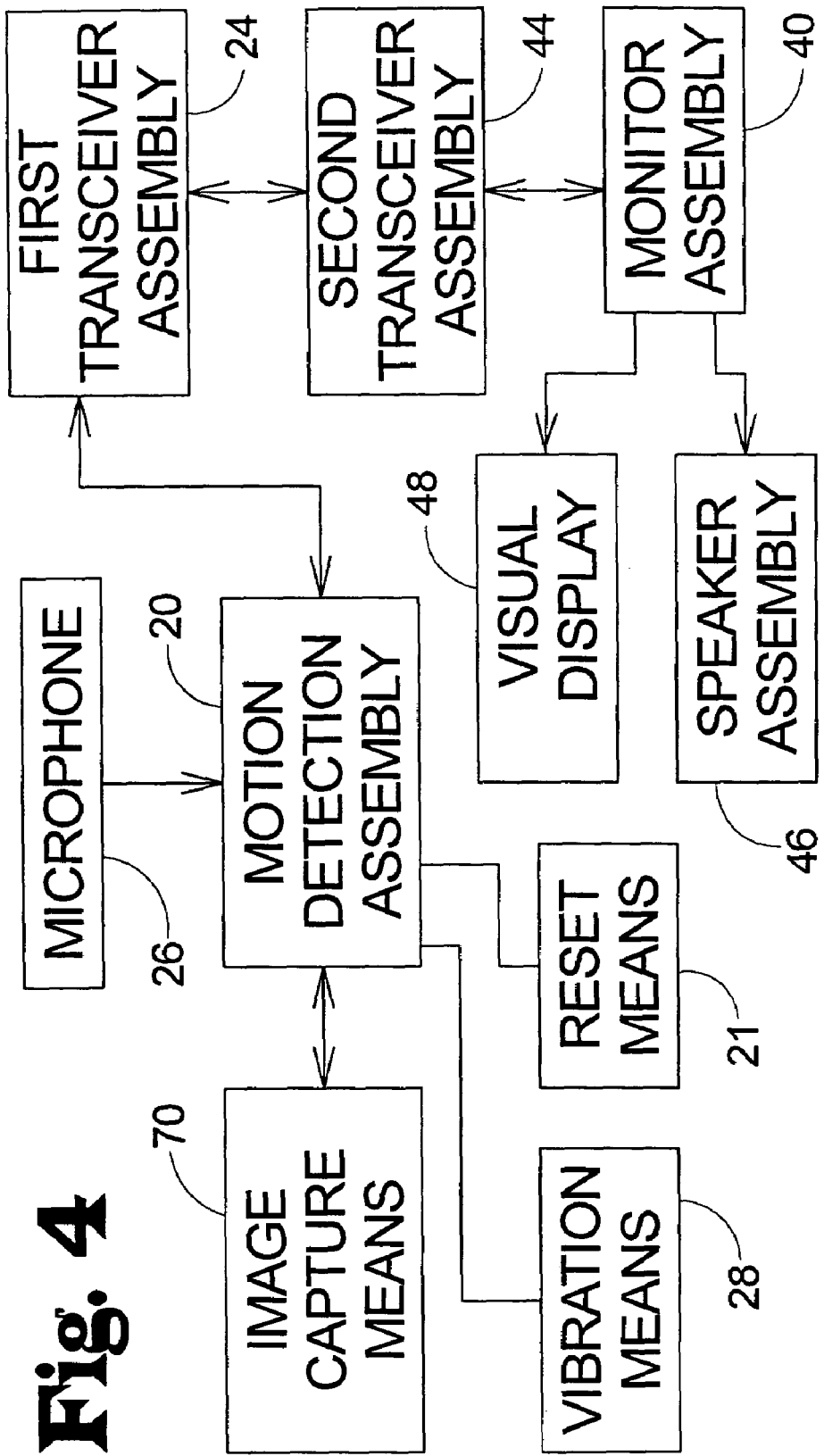
FIG. 4 is a schematic functional interconnect diagram of the present invention.
Figure 5:
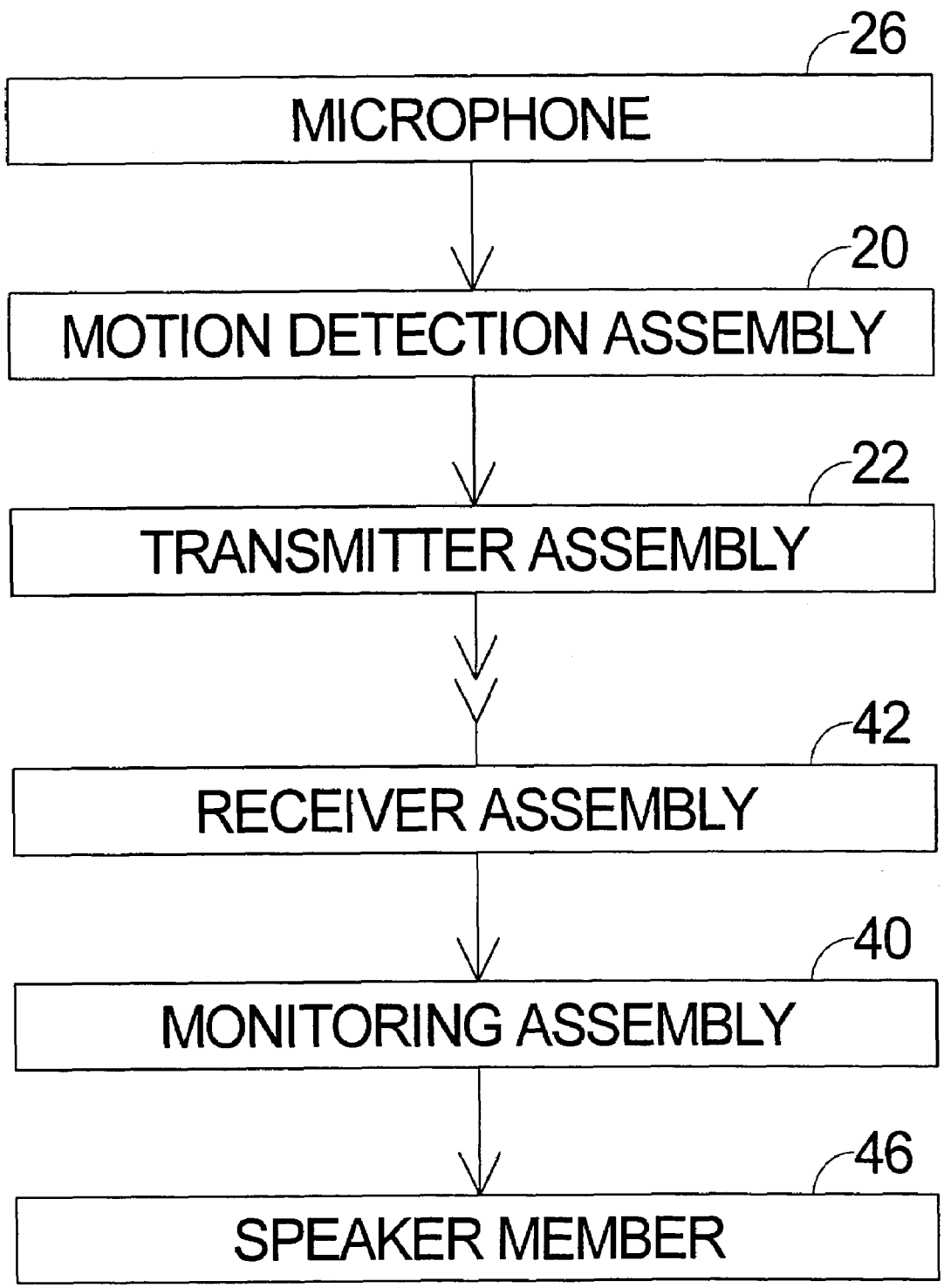
FIG. 5 is a schematic functional interconnect diagram of an embodiment of the present invention.

With reference now to the drawings, and in particular to FIGS. 1 through 5 thereof, a new child position monitoring system embodying the principles and concepts of the present invention and generally designated by the reference numeral 10 will be described.

As best illustrated in FIGS. 1 through 5, the child position monitoring system 10 generally a motion detection assembly 20, a coupling assembly 30, and a monitoring assembly 40.

The motion detection assembly 20 detects when the child rolls over. The motion detection assembly 20 includes a transmitter assembly 22 for sending a signal associated with motion detected.

The coupling assembly 30 is used for coupling the motion detection assembly 20 to the child. The coupling assembly 30 is preferably wearable by the child. Preferred versions of the coupling assembly include a body suit 32, a vest 34, or a belt 36.

The monitoring assembly 40 operationally interacts with the motion detection assembly 20. The monitoring assembly 40 provides an indication associated with motion detected by the motion detection assembly 20. The monitoring assembly 40 further comprises a receiver assembly 42 for receiving the signal associated with motion detected by the motion detection assembly 20.

A belt assembly 60 may be used for operationally coupling the monitoring assembly 40 to a user.

In at least one embodiment, an interconnection member 50 is operationally coupled between the motion detection assembly 20 and the monitoring assembly 40. The interconnection member 50 is elongate and flexible. The monitoring assembly 40 provides an indication associated with motion detected by the motion detecting assembly 20 when the interconnection member 50 is disconnected from either one of the motion detection assembly 20 or the monitoring assembly 40.

In a further embodiment, the indication associated with motion detected by the motion detecting assembly 20 further is an audio alarm.

In yet a further embodiment, the audio alarm is terminated upon reconnection of the interconnection member 50 between the motion detection assembly 20 and the monitoring assembly 40.

In still a further embodiment, the indication associated with motion, detected by the motion detection assembly 20 may be reset by actuating a reset means 21, such as a switch, operationally coupled to the motion detection assembly 20.

In an embodiment, the transmitter assembly 22 is designed for wireless transmission of the signal and the receiver assembly 42 being designed for wireless reception of the signal.

In even still a further embodiment the audio alarm may be terminated upon reception of a reset signal transmitted from the monitoring assembly 40 to the motion detection assembly 20.

In an embodiment the motion detection assembly 20 includes a first transceiver assembly 24 for sending a signal associated with motion detected and receiving signals from the monitoring assembly 40. Similarly, the monitoring assembly 40 further comprises a second transceiver assembly 44 for receiving the signal associated with motion detected by the motion detection assembly 20 and transmitting signals to the motion detection assembly 20.

A microphone 26 may be operationally coupled to the first transceiver assembly 24 for transmitting a representation of ambient sounds near the child, and a speaker member 46 may be operationally coupled to the second transceiver 44 for reproducing the representation of ambient sounds near the child.

A vibration means 28 may be operationally coupled to the motion detection assembly 20 to provide a tactile stimulation to the child. A wide variety of vibration means are known in the art including reed vibrators, offset weight and motor arrangements, and other suitable devices.

In an embodiment the vibration means 28 is actuated by a vibration signal transmitted from the second transceiver assembly 44 and received by the first transceiver assembly 24. Thus, the user may selectively control the tactile stimulation provided to the child.

In at least one embodiment, the system further comprises an image capture means 70 used in conjunction with the monitoring assembly 40. The image capture means 70 selectively captures at least one image of a child coupled to the motion detection assembly. Preferably, the image capture means is a video capture device for capturing a video image of the child. The video capture may be on a continuous, periodic, or as requested basis. Although a video capture device is preferred, a still image capture device may also be used with satisfactory results. The captured image may be routed to the transmitter assembly 22 or first transceiver for sending a representation of the captured image to the monitoring assembly for use by a care-giving user. The monitoring assembly may include a visual display 48 for providing a visual signal associated with the representation of the captured image. Additionally, the image capture device 70 may include a communications port to communicate with a personal computer. A wide variety of communications ports may be used with satisfactory results including but not limited to USB, Serial, Parallel, Firewire, wireless or other suitable devices.

In use, the coupling means is place on the child to be monitored, and the motion detection assembly is activated. If the interconnection member is to be used, then the interconnection member is coupled between the motion detection assembly and the monitoring assembly. The monitoring assembly may be coupled to the user. The monitoring assembly is activated. Upon the child rolling, the motion detection assembly transmits a signal, either wirelessly or through the interconnection member to the monitoring assembly which provides and indication of the child's movement. The user may then reposition and or relocate the child to prevent injury.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A child position monitoring system for detecting movement of a child, the system comprising:
   a motion detection assembly including a coupling assembly configured to be wearable by a child on the child's body for detecting when the child rolls over; and
   a monitoring assembly configured to be wearable by a person on the person's body, the monitoring assembly being configured to operationally interact with said motion detection assembly, said monitoring assembly providing an indication when motion is detected by said motion detection assembly;
   an interconnection member physically linking the coupling assembly of said motion detecting assembly to said monitoring assembly.

2. The system of claim 1, wherein said coupling assembly comprises a coupling member selected from the group of coupling members consisting of a body suit, a vest, and a belt.

3. The system of claim 1, further comprising:
   said motion detection assembly includes a transmitter assembly for sending a signal associated with motion detected;
   said monitoring assembly further comprises a receiver assembly for receiving said signal associated with motion detected by said motion detection assembly.

4. The system of claim 3, wherein said transmitter assembly is capable of wireless transmission of said signal and said receiver assembly is capable of wireless reception of said signal.

5. A child position monitoring system for detecting movement of a child, the system comprising:
   a motion detection assembly including a coupling assembly configured to be wearable by a child on the child's body for detecting when the child rolls over;
   a monitoring assembly configured to be wearable by a person on the person's body, the monitoring assembly being configured to operationally interact with said motion detection assembly, said monitoring assembly providing an indication when motion is detected by said motion detection assembly; and
   a belt assembly for operationally coupling said monitoring assembly to a user.

6. A child position monitoring system for detecting movement of a child, the system comprising:
   a motion detection assembly, said motion detection assembly detecting when the child rolls over, said motion detection assembly includes a transmitter assembly for sending a signal associated with motion detected;
   a coupling assembly for coupling said motion detection assembly to the child, said coupling assembly being wearable by the child;
   said coupling assembly comprises a coupling member selected from the group of coupling members consisting of a body suit, a vest, and a belt; and
   a monitoring assembly operationally interacting with said motion detection assembly, said monitoring assembly providing an indication associated with motion detected by said motion detection assembly; said monitoring assembly further comprises a receiver assembly for receiving said signal associated with motion detected by said motion detection assembly;
a belt assembly for operationally coupling said monitoring assembly to a user;
an interconnection member operationally coupled between said motion detection assembly and said monitoring assembly, said interconnection member being elongate and flexible;
said monitoring assembly providing an indication associated with motion detected by said motion detecting assembly when said interconnection member is disconnected from either one of said motion detection assembly and said monitoring assembly.

7. The system of claim 6, wherein said indication associated with motion detected by said motion detecting assembly further comprises an audio alarm.

8. The system of claim 7, wherein said audio alarm is terminated upon reconnection of said interconnection member between said motion detection assembly and said monitoring assembly.

9. The system of claim 6, wherein said transmitter assembly being adapted for wireless transmission of said signal and said receiver assembly being adapted for wireless reception of said signal.

10. The system of claim 9, wherein said indication associated with motion detected by said motion detecting assembly further comprises an audio alarm.

11. The system of claim 6, wherein said indication associated with motion detected by said motion detection assembly being reset by actuating a reset means operationally coupled to said motion detection assembly.

12. The system of claim 1, further comprising:
said coupling assembly comprises a coupling member selected from the group of coupling members consisting of a body suit, a vest, and a belt;
said motion detection assembly includes a first transceiver assembly for sending a signal associated with motion detected and receiving signals from said monitoring assembly; and
said monitoring assembly further comprises a second transceiver assembly for receiving said signal associated with motion detected by said motion detection assembly and transmitting signals to said motion detection assembly.

13. The system of claim 12, further comprising:
a microphone operationally coupled to said first transceiver assembly for transmitting a representation of ambient sounds near the child; and
a speaker member operationally coupled to said second transceiver for reproducing said representation of ambient sounds near the child.

14. The system of claim 13, wherein said indication associated with motion detected by said motion detecting assembly further comprises an audio alarm.

15. The system of claim 14, wherein said audio alarm is terminated upon reception of a reset signal transmitted from said monitoring assembly to said motion detection assembly.

16. The system of claim 14 further comprising:
a vibration means operationally coupled to said motion detection means, said vibration means providing a tactile stimulation to the child;
said vibration means being actuated by a vibration signal transmitted from said second transceiver assembly and received by said first transceiver assembly whereby the user may selectively control the tactile stimulation provided to the child.

17. The system of claim 14, further comprising:
an image capture means operationally interacting with said motion detection assembly, said image capture means selectively capturing at least one image associated with a child coupled to said motion detection assembly, said image capture means being operationally coupled to said first transceiver for routing a representation of said at least one image to said monitoring assembly; and
a visual display operationally coupled to said monitoring assembly, said visual display providing a visual signal associated with said representation of said at least one image to a monitoring user.

18. The system of claim 5, wherein said coupling assembly comprises a coupling member selected from the group of coupling members consisting of a body suit, a vest, and a belt;
said motion detection assembly includes a transmitter assembly for sending a signal associated with motion detected;
said monitoring assembly further comprises a receiver assembly for receiving said signal associated with motion detected by said motion detection assembly;
wherein said transmitter assembly is capable of wireless transmission of said signal and said receiver assembly is capable of wireless reception of said signal;
said motion detection assembly includes a first transceiver assembly for sending a signal associated with motion detected and receiving signals from said monitoring assembly;
said monitoring assembly further comprises a second transceiver assembly for receiving said signal associated with motion detected by said motion detection assembly and transmitting signals to said motion detection assembly;
a microphone operationally coupled to said first transceiver assembly for transmitting a representation of ambient sounds near the child;
a speaker member operationally coupled to said second transceiver for reproducing said representation of ambient sounds near the child;
wherein said indication associated with motion detected by said motion detecting assembly further comprises an audio alarm;
wherein said audio alarm is terminated upon reception of a reset signal transmitted from said monitoring assembly to said motion detection assembly;
a vibration means operationally coupled to said motion detection means, said vibration means providing a tactile stimulation to the child;
said vibration means being actuated by a vibration signal transmitted from said second transceiver assembly and received by said first transceiver assembly whereby the user may selectively control the tactile stimulation provided to the child;
an image capture means operationally interacting with said motion detection assembly, said image capture means selectively capturing at least one image associated with a child coupled to said motion detection assembly, said image capture means being operationally coupled to said first transceiver for routing a representation of said at least one image to said monitoring assembly;
a visual display operationally coupled to said monitoring assembly, said visual display providing a visual signal associated with said representation of said at least one image to a monitoring user.

* * * * *